United States Patent [19]

Karvinen et al.

[11] Patent Number: 5,498,738
[45] Date of Patent: Mar. 12, 1996

[54] METHOD FOR THE PREPARATION OF A NOVEL A-RING PRECURSOR FOR TAXOIDS AND NOVEL INTERMEDIATES

[76] Inventors: Esko Karvinen, Järvitie 4 E 43, FIN-90550 Oulu, Finland; Ari Koskinen, Lepikkotie 2 A 1,, FIN-90460 Oulunsalo, Finland

[21] Appl. No.: 266,557

[22] Filed: Jun. 28, 1994

[51] Int. Cl.⁶ .................. C07F 7/08; C07F 7/18
[52] U.S. Cl. ............. 556/441; 560/231; 560/249; 560/259; 554/77; 554/124; 554/229
[58] Field of Search ............ 556/441; 560/259, 560/231, 249; 554/77, 124, 229

[56] References Cited

U.S. PATENT DOCUMENTS

| | | | |
|---|---|---|---|
| 4,190,561 | 2/1980 | Auger et al. | 560/259 X |
| 4,550,211 | 10/1985 | Janitschke et al. | 560/259 X |
| 4,609,491 | 9/1986 | Schenk | 560/259 X |
| 4,876,399 | 10/1989 | Holton et al. | 556/441 X |
| 5,234,902 | 8/1993 | Levorse | 560/259 X |

FOREIGN PATENT DOCUMENTS 164929 7/1989 Ind..

OTHER PUBLICATIONS

Holton et al., J. Am. Chem. Soc., 1994, No. 116, pp. 1597–1598, "First Total Synthesis of Taxol. 1. Functionalization of B Ring".
Holton et al., J. Am. Chem. Soc., 1994, No. 116, pp. 1599–1600, "First Total Synthesis of Taxol. 2. Completion of the C and D Rings".
Nicolaou et al., Letters to Nature, vol. 367, 17 Feb. 1994, pp. 630–634, "Total synthesis of taxol".
Cainelli et al., J. C. S. Perkin I, 1979 pp. 1597–1599, "Synthesis of Compounds Containing Isoprene Unit; a Stereospecific Synthesis of β–Ionilideneacetic . . . ".
Konst et al., Tetrahedron Letters, No. 36, 1974, pp. 3175–3178, "A Convenient Synthesis of Safranal".
Rüttimann et al., Helvetica Chimica Acta. vol. 63, 1980, pp. 1456–1462, "154. Synthese von optisch aktiven, natürlichen Carotinoiden und . . . ".
Luche et al., J. Am. Chem. Soc., 101:19, Sep. 12, 1979, pp. 5848–5849, "Lanthanoids in Organic Synthesis. 5. Selective Reductions of Ketones in the Presence of Aldehydes".
Büchi et al., J. Org. Chem., vol. 37, No. 25, 1972, "Oxidation Products of Ethyl α–Safranate".
Lipshutz et al., Synlett, Sep. 1989, pp. 64–66, "1,4–Reductions of α,β–Unsaturated Ketones and Aldehydes via in situ Generated Hydridocuprates".

*Primary Examiner*—Paul F. Shaver
*Attorney, Agent, or Firm*—Ronald J. Kubovcik

[57] ABSTRACT

The present invention a process for the preparation of a compound of the formula (X) useful as precursor for the A-ring in taxanes

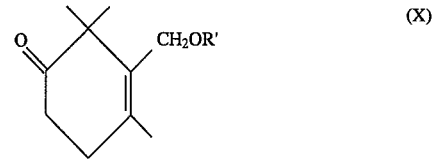
(X)

wherein R' is an

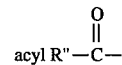
acyl R"—C— in which R" is a linear, branched or cyclic alkyl group of 1 to 10 carbon atoms. The invention further relates to the novel compound (X) and to novel intermediates in said process.

12 Claims, No Drawings

METHOD FOR THE PREPARATION OF A NOVEL A-RING PRECURSOR FOR TAXOIDS AND NOVEL INTERMEDIATES

FIELD OF THE INVENTION

The present invention provides a method for the preparation of a novel A-ring precursor for the ring system of taxoids. The invention provides further novel intermediates useful in said method.

BACKGROUND OF THE INVENTION

The publications and other materials used herein to illuminate the background of the invention, and in particular, cases to provide additional details respecting the practice, are incorporated by reference.

Taxoids or taxanes are highly complex diterpenes many of which exhibit promising antineoplastic activity. The anticancer active compound taxol is the most frequently cited taxane derivative in the literature. This compound was several decades ago isolated from the bark of the Pacific Yew (Taxus brevifolia) (Wani M C et al., J Am Chem Soc 1971, 93, 2325). Taxol has shown high activity against many tumor cell line systems. It has shown excellent activity, particularly in the treatment of advanced ovarian cancer, either as such or in combination with other anti-cancer drugs. It has also been succesful in the treatment of breast cancer, lung cancer, melanoma and several other cancers, too. (For clinical usage of taxol, see Rowinsky E et al., J Natl Cancer Inst 1990; 82:1247 –1259).

The taxol molecule (1) is shown in Scheme 1. The molecule comprises a side chain attached to a complex ring system built up of the A-, B-, C and D-rings. Synthetic approaches to taxol and its derivatives have been extensively described in the literature (see for example Boa, Jenkins and Lawrence, Contemporary Organic Synthesis, 1994, 1, 47; Nicolaou K C et al., Angew Chem Int Ed Engl 1994, 33, 15). Despite extensive attempts, no successful total synthesis of taxol has been published until very recently (Nicolaou K C et al., Nature 1994, 367, 630; Holton R A et al., J Am Chem Soc 1994, 116, 1597; Holton R A et al., ibid, 1994, 116, 1599). To avoid the problem of direct extraction of taxol from the bark of yew trees, semisynthetic methods for the production of taxol have also been developed. The compound 10-deacetylbaccatin III (compound 2 in Scheme 2), which constitutes the ring system of taxol, can be derived from renewable needles and twigs of the yew tree. The introduction of the side chain into the 13-position of 10-deacetylbaccatin yields taxol or derivatives thereof.

The advent of chemotherapy based on taxol and its derivatives has, however, been hampered by shortcomings relating to their limited availability. Another disadvantage, particularly relating to taxol, is the low aqueous solubility. As a result of the low water solubility, formulations have been made that based on surfactants giving rise to adverse effects in some patients. Thus, there is a great need to develop a synthesis that could be used for the large scale production of taxol as well as for the production of more water soluble taxane derivatives.

Both of the problems concerning the limited availability of taxol as well as its low water solubility can be solved through the development of a sufficiently flexible entry into taxol and its structural analogues. The inventors of the present invention have recently initiated a program with this as a major goal (Koskinen A M P et al., J Chem Soc Chem Commun, 1994, 21). Scheme 2 discloses the structure of the some taxanes with anti-cancer activity as well as 10-deacetylbaccatin III and baccatin III, compounds useful as starting materials in the semi-synthesis of taxol or its analogues. The structure of the side chain is responsible for the water solubility of the molecule. Compounds 5 to 8 (Scheme 2) have proved to have higher solubility in water than taxol itself. (See Nicolaou K C et al., Angew Chem Int Ed Engl 1994, 33, 15).

SUMMARY OF THE INVENTION

The present invention relates a process for the preparation of a compound of the formula (X) useful as precursor for the A-ring in taxanes

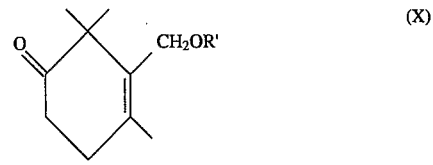

wherein R' is an

in which R" is a linear, branched or cyclic alkyl group of 1 to 10 carbon atoms. The process comprises the steps of a) reacting the alcohol of the formula (VI) (for formulae see Scheme 3) with the acid chloride R" COCl wherein R" is a linear, branched or cyclic alkyl group of 1 to 10 carbon atoms, in pyridine and a chlorinated hydrocarbon solvent, preferably dichloromethane, chloroform or carbon tetrachloride, to give the corresponding ester (VII), b) oxidizing the ester (VII) with selenium dioxide in dioxane to give the corresponding enone (VIII), c) reducing the enone (VIII)
  i) either by treating said enone (VIII) with a mixture comprising cuprous iodide, tributyl tinhydride $((C_4H_9)_3SnH)$, lithium chloride and trimethylsilylchloride (TMSCl) to give the compound (IX) and hydrolysing the compound (IX) to a compound of formula (X) or
  ii) by catalytical hydrogenation of the enone (VIII) over a supported Pd catalyst to give the compound of formula ( X ) . In the process R' is preferably

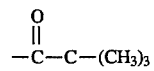

The novel compounds of formulae (X) and (VII) to (IX) are also within the scope of the invention.

DETAILED DESCRIPTION OF THE INVENTION

The novel process of this invention as well as the novel A-ring precursor obtained by said process and the novel intermediates used therein are disclosed in Scheme 3. Scheme 3 illustrates further a useful method for the preparation of safranal, the starting material used in the process according to this invention.

Safranal (compound V) (Kuhn R and Wendt G, Ber. 1936, 69, 1549) is the major constituent of saffron oil (Zarghami N S and Heinz D E, Phytochemistry 1971, 10, 2755).

Safranal can also be prepared from the inexpensive citral (compound I) in two or three steps. Treatment of a mixture of E- and Z-citrals (compound I) (Lancaster Synthesis) with aniline to give the Schiff base (Colombi et al., Helv Chim Acta 1951, 34, 265; Henbest H Bet al., J Chem Soc, 1952, 1154) followed by cyclization gives a mixture of α- β-cyclocitrals (compounds IIa and IIb) (Gedye R Net al., Can J Chem, 1971, 49, 1764). This mixture can be transformed to safranal by alternative methods disclosed in the literature. Initially, the most appealing approach seemed to be the one pot preparation (Kumar et al., Indian Pat. IN 164,929; CA 1990, 113, 132552t) where the mixture of cyclocitrals was first treated with bromine in DMF at +5° C. followed by treatment with lithium carbonate at room temperature to effect the first dehydrobromination followed by heating at 100°–110° C. overnight. However, the inventors of the present invention noted that the method gave a product contaminated with impurities which were extremely difficult to separate. The second method that was tried was a combination of two literature methods (see Cainelli Get al., J Chem Soc, Perkin I 1979, 1597 and Könst W M Bet al., Tetrahedron Lett., 1974, 3175). Treatment of the mixture of cyclocitrals (IIa and IIb) with bromine at –60° C. in dichloromethane in the presence of calcium carbonate (Cainelli Get al., J Chem Soc, Perkin I 1979, 1597) gave the crude dibromide (III) which was dehydrobrominated with 1 eq of collidine in boiling toluene (Könst W M Bet al., Tetrahedron Lett., 1974, 3175) to give the allylic bromide (IV) in 76% yield over two steps. Dehydrobromination in boiling collidine followed by steam distillation and flash cromatography gave pure safranal (V) but the yield was poor. Therefore yet another combination of methods was tried. After bromination at –60° C. in dichloromethane as above the dibromide (III) thus obtained was dissolved in DMF (dimethylformamide) and treated with lithium carbonate in DMF followed by heating overnight at 100°–110° C. In this way safranal was obtained in 72% yield after distillation. The next step was the chemoselective reduction of the conjugated aldehyde (V) to the corresponding allylic alcohol (VI). Of the various reducing agents that were tested $NaBH_4/CeCl_3$ in aqueous ethanol at –15° C. was the best giving the desired alcohol (compound VI) (Röuttimann A and Mayer H, Helv Chimica Acta 1980, 63, 1456) in a high yield (Luche J-L and Gemal A L J Am Chem Soc 1979, 101, 5848). The alcohol (VI) is rather unstable and therefore it is preferably transformed without further purification to the ester (VII) by treatment with an acid chloride, preferably pivaloyl chloride ($(CH_3)_3$—CCOCl) in pyridine and a chlorinated hydrocarbon solvent, preferably dichloromethane, chloroform or carbon tetrachloride. The ester (VII) can be transformed to the corresponding enone (VIII) by oxidation with selenium dioxide in dioxane (Büchi Get al., J Org Chem 1972, 37, 4192). The enone (VIII) is finally reduced to the ketone of formula (X) e.g. by hydrogenation over supported Pd catalyst. More preferably, the reduction is performed by treating the enone (VIII) with a mixture comprising cuprous iodide, tributyl tinhydride ($(C_4H_9)_3SnH$), lithium chloride and trimethylsilylchloride (TMSCl) (Lipshutz B H et al., Synlett, 1989, 64) to give the compound (IX) followed by hydrolysing the compound (IX) to the ketone of formula (X).

All the compounds of formulas (VII) to (X) are novel except for the compound (X) wherein R' is —CO—$CH_3$.

The invention will be illuminated by the following non-restrictive examples.

General procedures: The solvents were dried over appropriate drying agents (Perrin, D.D.; Armarego, W.L.F. Purification of Laboratory Chemicals 3rd ed., Pergamon Press, 1988). Thin layer chromatography was performed on silica gel 60 $F_{254}$ plates from Merck. Spots were visualized under UV light (254 nm) and by sparying with a 3% vanillin ethanol solution containing 1% $H_2SO_4$ or with a 1% phosphomolybdic acid ethanol solution followed by heating with heat gun. For flash chromatography silica gel 60(particle size 0.040–0.063 mm) from Merck was used. NMR spectra were recorded on a Bruker AM –200 spectrometer.

EXAMPLE 1

Compound VII (R'=pivaloyl) of Scheme 3

According to the procedure of Luche J-L and Gemal A L J Am Chem Soc 1979, 101, 5848, safranal (Compound V of Scheme 3) (0.504 g, 3.36 mmol) was dissolved in ethanol (20 ml) and the solution was cooled to –15° C. and water (34 ml) and $CeCl_3 \times 7H_2O$ (1.252 g, 3.36 mmol) were added. After 5 –10 min stirring sodium borohydride (0.190 g, 5.04 mmol) was added in one lot and stirring was continued until TLC showed that the starting material was consumed. After 16 min acetone (10 ml) was added and stirring was continued for 5 min. Brine (50 ml) and ether (50 ml) were then added and the phases were separated and the aqueous layer was extracted with ether. The combined extracts were washed with brine and dried over sodium sulfate. The solvent was evaporated and the residue dissolved in methylene chloride and dried again with sodium sulfate. Evaporation of the solvent gave 0.489 g of Compound VI of Scheme 3 as pale yellow oil which was used immediately in the next step without further purification. The crude product (0.489 g) was dissolved in methylene chloride (5 ml), pyridine (5 ml) was then added and the solution was stirred under argon at 0° C. Pivaloyl chloride (410 µl, 3.31 mmol) was added dropwise and the mixture was stirred overnight, during which time the bath was warmed to room temperature. The solvents were concentrated on a rotary evaporator (bath temperature about 30° C. ) and toluene was added and evaporation was repeated (this was done twice). The product was purified by flash chromatography to yield 0.732 g (92%) of Compound VII (R'=pivaloyl).

Alcohol (Compound VI):

$^1$H NMR (CDCl$_3$): δ5.77(2H, m), 4.24(2H, s), 2.08 (2H, d, J =2.4 Hz), 1.84 (3H, s), 1.08(6H, s).

$^{13}$C NMR (CDCl$_3$): δ137.3, 129.2, 129.0, 126.1, 58.8, 39.9, 33.2, 26.5, 17.9.

HRMS: found 152.1192 calcd for $C_{10}H_{16}O$, 152.1201.

Pivalate (Compound VII):

$^1$H NMR (CDCl$_3$): δ5.7–5.8 (2H, m), 4.68 (2H, s), 2.08 (2H, d, J=2.2 Hz), 1.81 (3H, s), 1.21 (9H, s), 1.02(6H, s).

$^{13}$C NMR (CDCl$_3$): δ178.7, 132.5, 131.3, 129.1, 126.7, 61.2, 39.9, 38.8, 33.1, 27.2, 26.3, 18.1.

HRMS: found 236.1747 calcd for $C_{15}H_{24}O_2$ 236.1776.

EXAMPLE 2

Compound VIII (R'=pivaloyl) of Scheme 3

Compound VII obtained in the foregoing example (2.36 g, 10 mmol) was dissolved in dioxan under argon and freshly sublimed selenium dioxide (1.17 g, 10.5 mmol) was added and the mixture was refluxed for 30 minutes. The cooled mixture was poured on water and extracted four times with ether. The combined extracts were washed with water and dried over sodium sulfate. Filtering and concentration gave the crude product which was purified by flash chromatography on silica (eluent 9:1 to 2:1 hexanes/MTBE) to give 914 mg (37 of the desired enone (Compound VIII).

$^1$H NMR (CDCl$_3$): δ6.92 (1H, d, J=9.8 Hz), 6.09 (1H, d, J=9.8 Hz), 4.71 (2H, s), 1.98 (3H, s), 1.22 (6H, s), 1.19 (9H, s).

$^{13}$C NMR (CDCl$_3$): δ204.7, 177.9, 146.2, 144.2, 129.0, 124.9, 59.8, 48.8, 38.6, 26.9, 23.9, 18.1.

HRMS: found 250.1551 calcd for C$_{15}$H$_{22}$O$_3$250.1569.

EXAMPLE 3

Compound X (R'=pivaloyl) of Scheme 3

CuI (0.103 g, 0.543 mmol) and LiCl (0.0542 g, 1.28 mmol) were dissolved in dry THF under argon and the solution was stirred at −55° C. to −60° C. The enone (Compound VIII from the foregoing example) (0.0533 g, 0.213 mmol) was added in 1.5 ml THF followed by trimethylsilyl chloride (145 μl, 1.14 mmol) and the mixture was stirred for 10 min. Tributyltin hydride (161 μl, 0.597 mmol) was added dropwise and the mixture was stirred for 2 h and 10 min during which time the mixture was allowed to warm to 0° C. The mixture was treated with 10% aqueous KF (1.6 ml). After the gas evolution had ceased ether was added. The ether layer was filtered through a pad of Celite and the solvents were evaporated. The residue was stirred with 10% aqueous KF for 30 min. Extraction with ether, washing whith brine and drying over sodium sulfate gave the crude product which was purified by flash chromatography (9:1 hexanes/MTBE). The first fractions (42 mg) contained the desired product as its trimethylsilyl enolether (Compound IX of Scheme 3) contaminated by a tributyltin compound. The later fractions gave 12 mg of 3:1 mixture (GC) of the desired ketone (Compound X) and an impurity. The mixture of the TMS-enol ether (Compound IX) and the tributyltin impurity was dissolved in methanol (2.5 ml) and 62 mg of citric acid monohydrate was added and the mixture was stirred for 5 h at room temperature. Evaporation of the solvent followed by flash chromatography gave 24 mg of the pure ketone (Compound X where R' is pivaloyl).

TMS-enol ether (Compound IX):

$^1$H NMR (CDCl$_3$): δ4.68 (1H, t, J=3.6 Hz), 4.60 (2H, s), 2.72 (2H, d, J=3.4 Hz), 1.69 (3H, s), 1.19 (9H, s), 1.10 (6H, s), 0.21 (9H, s).

$^{13}$C NMR (CDCl$_3$): δ6 178.8, 154.6, 132.2, 130.7, 97.1, 60.8, 39.0, 38.8, 33.0, 27.2, 25.4, 18.8, 0.4.

HRMS: found 324.2118 calcd for C$_{18}$H$_{32}$SiO$_3$324.2121.

Ketone (Compound X):

$^1$H NMR (CDCl$_3$): δ4.60 (2H, s), 2.44–2.59(4H, m), 1.79(3H, s), 1.19 (9H, s), 1.18 (6H, s).

$^{13}$C NMR (CDCl$_3$): δ214.3, 178.6, 135.9, 131.7, 60.7, 47.0, 38.8, 35.6, 31.8, 27.1, 24.5, 19.5.

It will be appreciated that the methods of the present invention can be incorporated in the form of a variety of embodiments, only a few of which are disclosed herein. It will be apparent for the artisan that other embodiments exist and do not depart from the spirit of the invention. Thus, the described embodiments are illustrative and should not be construed as restrictive.

Scheme 1

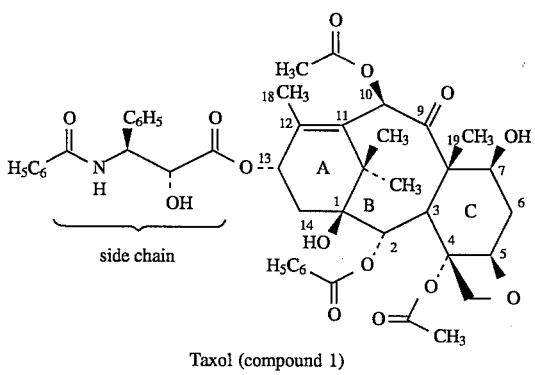

Taxol (compound 1)

Scheme 2

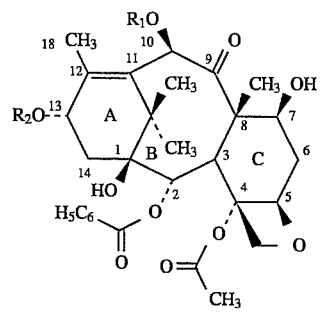

| Compound | R$_1$ | R$_2$ | R$_3$ |
|---|---|---|---|
| No 2 (10-deacetyl-baccatin III) | H | H | — |
| No 3 (baccatin III) | COCH$_3$ | H | — |

Scheme 2
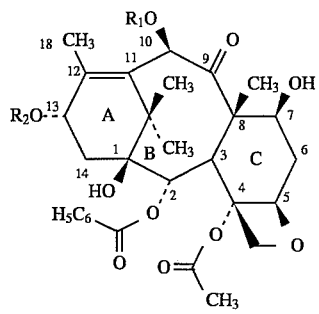
| Compound | $R_1$ | $R_2$ | $R_3$ |
|---|---|---|---|
| No 4 (taxotere) | H | (CH₃)₃—C—O—C(O)—NH—CH(C₆H₅)—CH(OH)—C(O)— | — |
| No 5 | COCH₃ | H₅C₆—C(O)—NH—CH(C₆H₅)—CH(OR₃)—C(O)— | CH₃—C(O)—(CH₂)ₙ—C(O)—O—N⁺H—(CH₂CH₂OH)₃  n = 1,2 |
| No 6 | COCH₃ | " | CH₃—C(O)—CH₂—C(O)—NH—(CH₂)₃—N⁺H(Me)₂ Cl⁻ |
| No 7 | COCH₃ | " | CH₃—C(O)—CH₂—CH₂—C(O)—ONa |
| No 8 | COCH₃ | " | CH₃—C(O)—CH₂—N⁺H(Et)₂ MeSO₂⁻ |
Scheme 3
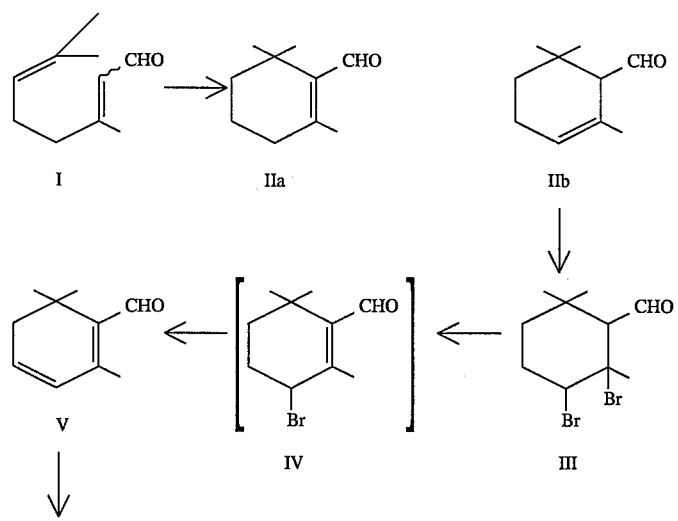

-continued
Scheme 3

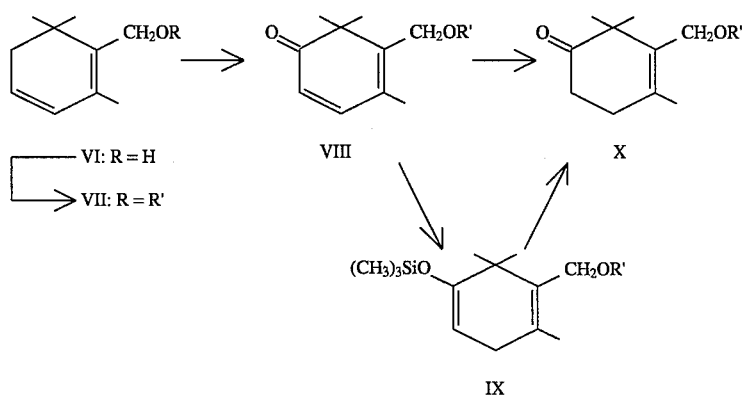

We claim:

1. A process for the preparation of a compound of the formula (X) useful as precursor for the A-ring in taxanes

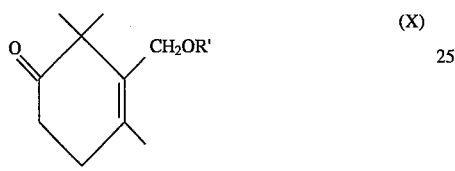 (X)

wherein R' is

in which R" is a linear, branched or cyclic alkyl group of 1 to 10 carbon atoms, which process comprises the steps of a) reacting the alcohol of the formula (VI)

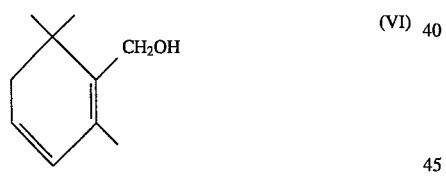 (VI)

with the acid chloride R"COCl, wherein R" is a linear, branched or cyclic alkyl group of 1 to 10 carbon atoms, in pyridine and a chlorinated hydrocarbon solvent, preferably dichloromethane, chloroform or carbon tetrachloride, to give the corresponding ester (VII)

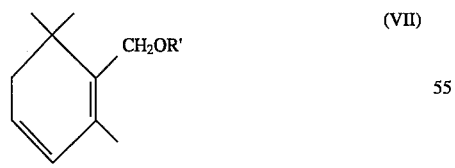 (VII)

wherein R' is

and R" is the same before, b) oxidizing the ester (VII) with selenium dioxide in dioxane to give the corresponding enone (VIII)

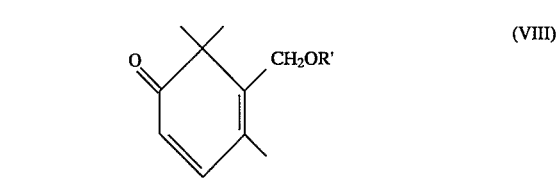 (VIII)

and c) reducing the enone (VIII)

i) either by treating said enone (VIII) with a mixture comprising cuprous iodide, tributyl tinhydride ((C$_4$H$_9$)$_3$SnH), lithium chloride and trimethylsilylchloride (TMSCl) to give the compound (IX)

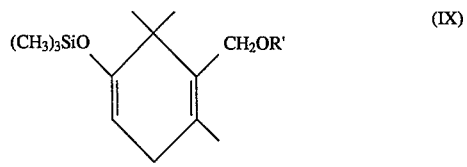 (IX)

and hydrolysing the compound (IX) to a compound of formula (X)

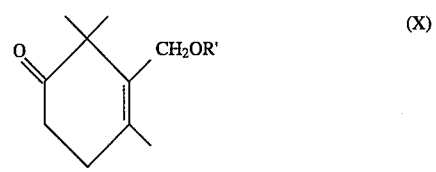 (X)

or ii) by catalytical hydrogenation of said enone (VIII) over a supported Pd catalyst to give the compound of formula (X)

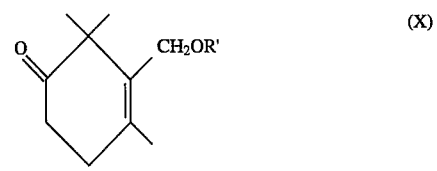 (X)

2. The process according to claim 1 wherein the alcohol (VI) is prepared by dissolving a dibromide of the formula (III)

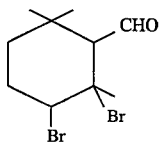 (III)

in dimethylformamide (DMF) and treating with lithium carbonate in DMF followed by heating to about 100°–110° C. for several hours to give the aldehyde (V)

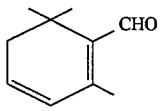 (V)

and reducing said aldehyde (V) to the corresponding alcohol (VI) which without further purification is esterified to the compound (VII) as described in claim 1.

3. The process according to claim 1 wherein R' is

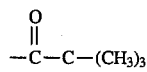

4. A compound of the formula (X) useful as precursor for the A-ring in taxanes

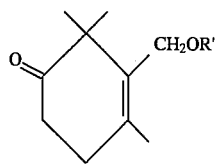 (X)

wherein R' is

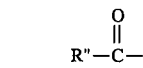

in which R" is a linear, branched or cyclic alkyl group of 2 to 10 carbon atoms.

5. A compound of the formula (VII)

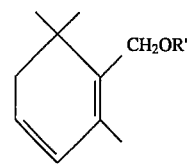 (VII)

wherein R' is

and R" is a linear, branched or cyclic alkyl group of 1 to 10 carbon atoms.

6. A compound of the formula (VIII)

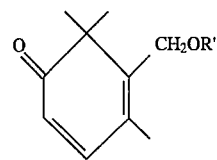 (VIII)

wherein R' is

and R" is a linear, branched or cyclic alkyl group of 1 to 10 carbon atoms.

7. A compound of the formula (IX)

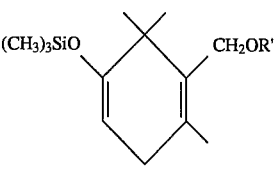 (IX)

wherein R' is

and R" is a linear, branched or cyclic alkyl group of 1 to 10 carbon atoms.

8. A compound according to claim 4 wherein R' is

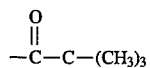

9. The process according to claim 2 wherein R' is

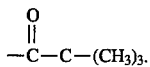

10. A compound according to claim 5 wherein R' is

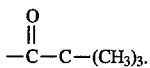

11. A compound according to claim 6 wherein R' is

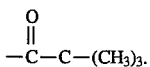

12. A compound according to claim 7 wherein R' is

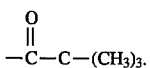

* * * * *